United States Patent [19]

Muegge et al.

[11] Patent Number: 4,722,095

[45] Date of Patent: Jan. 26, 1988

[54] METHOD FOR IDENTIFYING POROSITY AND DRILLING MUD INVASION OF A CORE SAMPLE FROM A SUBTERRANEAN FORMATION

[75] Inventors: Ernest L. Muegge, Grand Prairie; Jorge J. Faz, Dallas; Eve S. Sprunt, Farmers Branch, all of Tex.

[73] Assignee: Mobil Oil Corporation, New York, N.Y.

[21] Appl. No.: 872,341

[22] Filed: Jun. 9, 1986

[51] Int. Cl.[4] .................. G01N 23/06; G01V 5/00
[52] U.S. Cl. ................................. 378/4; 378/51; 250/252.1; 250/262; 250/269
[58] Field of Search .............. 378/4, 10, 51; 250/255, 250/269, 262, 253; 73/38, 61.4

[56] References Cited

U.S. PATENT DOCUMENTS

| | | | |
|---|---|---|---|
| 3,839,899 | 10/1974 | McMillen | 73/38 |
| 4,146,788 | 3/1979 | Mirkin et al. | 250/253 |
| 4,157,472 | 6/1979 | Beck, Jr. et al. | |
| 4,283,629 | 8/1981 | Habermehl et al. | |
| 4,399,509 | 8/1983 | Hounsfield | 364/414 |
| 4,422,177 | 12/1983 | Mastronardi et al. | 378/17 |
| 4,571,491 | 2/1986 | Vinegar et al. | 378/207 |
| 4,649,483 | 3/1987 | Dixon | 250/256 |

OTHER PUBLICATIONS

"Computed Tomographic Analysis of Meteorite Inclusions", by J. R. Arnold, et al., Science, vol. 219, Jan. 1983, pp. 383–384.

Primary Examiner—Carolyn E. Fields
Assistant Examiner—Joseph A. Hynds
Attorney, Agent, or Firm—Alexander J. McKillop; Michael G. Gilman; George W. Hager, Jr.

[57] ABSTRACT

A core sample invaded by drilling mud is scanned with X-rays and computed tomographic images are produced. The images are calibrated to a density scale based on the barite content of the drilling mud. The mud solid volume in the pores of the core sample are determined from the density contrast created in the computed tomographic images by the presence of barite in the core sample. This mud solid volume is used to provide a corrected porosity measurement on the core sample.

4 Claims, 2 Drawing Figures

METHOD FOR IDENTIFYING POROSITY AND DRILLING MUD INVASION OF A CORE SAMPLE FROM A SUBTERRANEAN FORMATION

BACKGROUND OF THE INVENTION

Computed tomography (CT) technology has been in use in the medical field for a number of years. CT scanning instruments produce a cross-sectional view through the subject material along any chosen axis. The advantages of CT scanning over conventional radiography is found in its ability to display the electron density variations within the object scanned in a two-dimensional X-ray image. In medical CT scanners, an X-ray source and a detector array circle a patient in a period of about 2 to 9 seconds and produces an image with maximum resolutions of 0.25 mm in the X-Y plane. This plane can be moved in discrete intervals to obtain information in three dimensions. For more details of such medical CT scanners, reference may be made to U.S. Pat. No. 4,157,472 to Beck, Jr. and Barrett (Assignee: General Electric Company) and U.S. Pat. No. 4,399,509 to Hounsfield (Assignee: EMI Limited).

Many other applications of CT scanning can also be made. For example, in an article entitled, "Computed Tomographic Analysis of Meteorite Inclusions", *Science*, pps. 383-384, Jan. 28, 1983, there is described the non-destructing testing of meteorites for isotopic anomalies in calcium- and aluminum-rich inclusions of heterogeneous materials, such as Allende. The CT scanning equipment described in such article is the Deltascan 2020 from Technicare. In a further application, CT scanning has been applied to the non-destructive testing of wood materials, such as for disease in living trees, see U.S. Pat. No. 4,283,629 to Habermehl. In a yet further application, CT scanning has been applied to the examination of non-living objects, such as motors, ingots, pipes, etc., see U.S. Pat. No. 4,422,177 to Mastronardi, et al. (Assignee: American Science and Engineering, Inc.).

More recently, the CT scanning technology has been applied to the field of energy research for examining the interior of stationary or slowly changing earth materials such as coal, shale and drilling cores. Processes involved in coal gasification and combustion have been monitored using time-lapse CT imagery to observe changes in density (e.g., thermal expansion, fracturing emission of gases, consumption by combustion) during progressive heating in a controlled atmosphere. Core flooding experiments can now be carried out with CT scanning to aid in enhanced oil recovery and fluid mobility control. For example, the permeability of materials within core samples to various fluids at varying conditions of temperature and pressure can be determined. Such experiments might involve flushing a fluid through a core sample and monitoring the shape of the fluid fronts. By subtracting the images of the cores before and after flooding, the exact shapes of the fluid front are determined. Such core flood experiments allows the interior of the core sample to be observed without disturbing the sample. The sweep efficiency and flow paths of fluids of interest may now be studied on the scale of millimeters. The penetration of X-rays allows experiments to be performed with up to 4-inch diameter core samples.

Drilling fluids can be analyzed by CT scanning as such fluids are characterized by high-density brines, various organics and several compositionally different weighting agents. Shale oil recovery can be aided as CT scanning could detect penetration by solvents and could directly measure structure changes on retorting. Rock fractures can be identified.

SUMMARY OF THE INVENTION

The present invention is directed to a method for identifying the porosity and drilling mud invasion of a core sample from a subterranean formation. The mud filtrate is removed from the core sample, after which measurements are made of the pore volume, bulk volume and mud solid volume of the core sample. The porosity of the core sample is determined from such measurements.

In measuring mud solid volume, the core sample is scanned with X-rays. The X-ray scanning is calibrated to a density scale based on the barite content of the drilling mud. Computed tomographic images are recorded, and the mud solid volume is determined from the density contrast created in such images by the presence of barite in the core sample, the barite having a higher grain density than the remaining minerals forming the core sample. This X-ray scanning is preferably calibrated by adjusting the computed tomographic number scale in Hounsfield units to a zero level based on the numerical measure of the X-ray absorption property of barite.

In a more specific aspect, a gas is supplied to the core sample at a first pressure. The gas is thereafter allowed to expand from the core sample until equilibrium is reached. The volume of the gas which expands from the core sample is measured. A second pressure is measured in the core sample after the gas has expanded. The pore volume of the core sample is determined from such first and second pressures and such measured gas volume. Bulk volume of the core sample is measured. Porosity of the core sample is determined from the ratio of the pore volume to the bulk volume. The core sample is scanned with X-rays and computed tomographic images produced. The concentration of drilling mud solid in the core sample is identified from the density effect of the drilling mud solid on the computed tomographic images. The porosity determination is corrected for the volumetric concentration of drilling mud solid in the pore spaces of the core sample.

DESCRIPTION OF THE PREFERRED EMBODIMENT

In the production of minerals, e.g., oil and gas, certain lithological properties of a subterranean reservoir must be determined. Two of the most important of these properties are the porosity and permeability of the reservoir. Porosity of a material is the ratio of the aggregate volume of its void or pore spaces (i.e., pore volume) to its gross bulk volume and, in the case of an oil or gas reservoir, is a measure of the capacity within the reservoir rock which is available for storing oil or gas. Permeability of a material is a measure of the ability of the material to transmit fluids through its pore spaces and is inversely proportional to the flow resistance offered by the material. Another important parameter is pore compressibility, which is change in porosity, or pore and bulk volume, as a function of pressure.

Normally, these parameters are determined by taking core samples from the reservoir and carrying out well-defined measurement techniques on the samples. There are several techniques available for making such measurements, many of which are described in PETROLEUM PRODUCTION ENGINEERING—DEVELOPMENT by L. C. Uren, Fourth Edition, McGraw-Hill Book Company, Inc., 1956, pps. 660–669. Another standard reference is American Petroleum Institute, *API Recommended Practice for Core-Analysis Procedure*, API RP 40, 1960, 55 pp.

U.S. Pat. No. 3,839,899 describes both method and apparatus for measuring both the pore volume and the bulk volume of the core sample, and determining porosity from the ratio of the pore volume to the bulk volume. However, mud solid invasion of a core sample can be a severe problem in providing an accurate porosity determination. Mud solid, principally the barite content of drilling mud, cannot be removed along with mud filtrate by conventional core cleaning techniques. It is, therefore, a specific aspect of the present invention to identify and volumetrically quantify any such barite content in core samples by use of CT scanning so that a conventional porosity determination, such as by the method of U.S. Pat. No. 3,839,899, can be corrected for the pore volume occupied by such barite.

Figure 1:
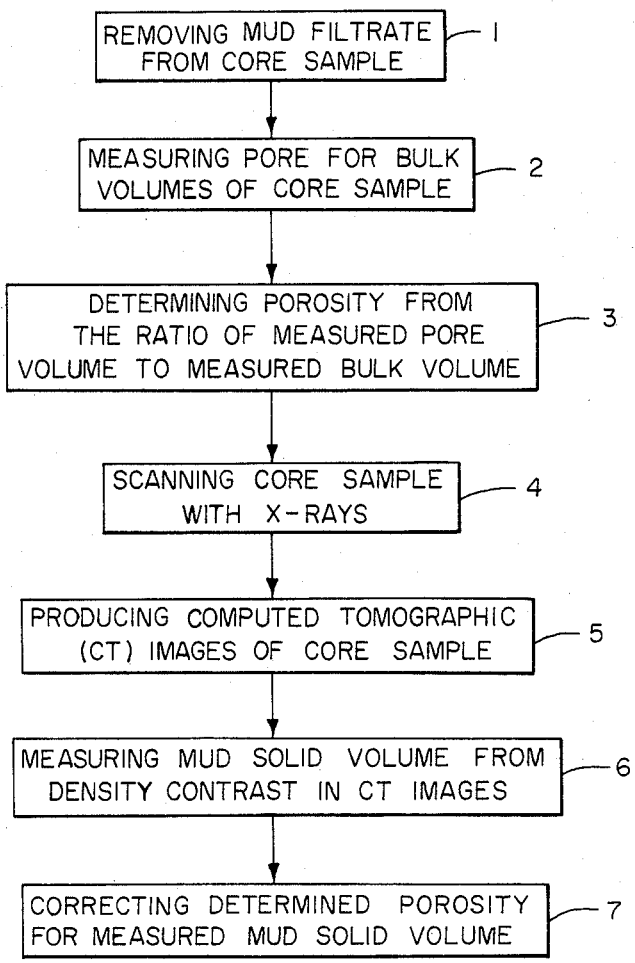
FIG. 1 is a flow chart depicting the steps involved in identifying the porosity and drillings mud invasion of a core sample in accordance with the present invention.

Referring to FIG 1, the mud filtrate in the core sample is removed at step 1 and the pore and bulk volumes are measured at step 2. To measure pore volume, a gas is supplied to the core sample at a first pressure $P_1$. The gas is then allowed to expand from the core sample until equilibrium pressure is reached. The volume of the gas that expands from the core sample is measured. A second pressure $P_2$ in the core sample is measured after the gas has expanded. Pore volume is then determined from these first and second pressures and the measured gas volume. For more details as to this pore volume measurement and its use in porosity determination at step 3, reference may be made to the aforementioned U.S. Pat. No. 3,839,899, the teaching of which is incorporated by reference.

Figure 2:
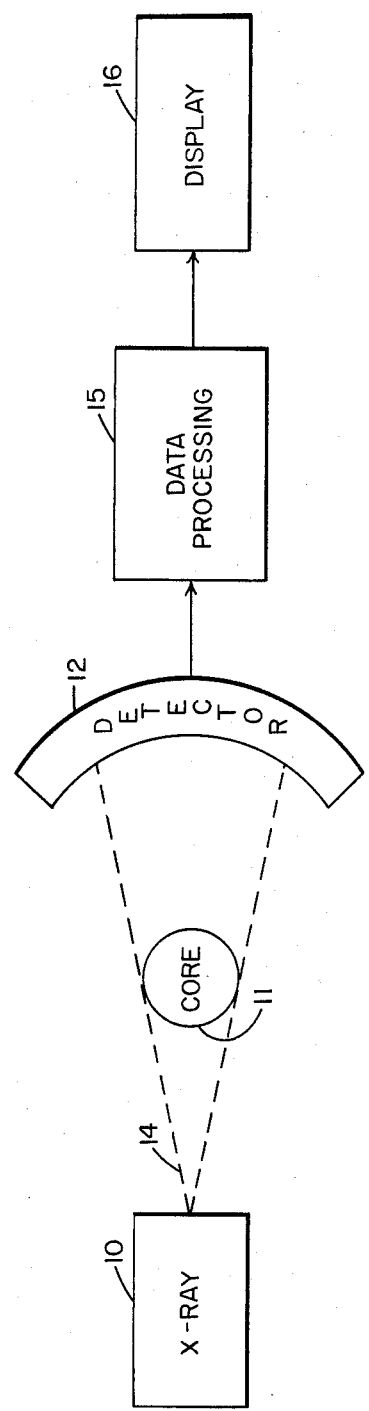
FIG. 2 is a pictorial view of a CT scanning system for use in scanning a sample of porous material with X-rays in accordance with the method of the present invention.

CT scanning of the core sample is next carried out at step 4 to correct the porosity determination for the presence of barite from the drilling mud in the core sample pore spaces. Referring now to FIG. 2, X-ray energy provided by the X-ray tube 10 passes through the core sample 11 and falls on the detector array 12. Rotation of the core sample within the X-ray fan beam 14 is provided by suitable gantry means (not shown). In an alternative embodiment, the core sample 11 may remain stationary and the gantry may be used to rotate the X-ray tube 10 and detector 12 about the core sample. In medical applications, CT scanning rates are usually in the order of 2 to 9 seconds. However, patient dose limitations are of no concern in the present application, and scan times of the core sample can be up to 30 seconds per scan. The output of the detector 12 is passed through the data processing unit 15 to the display unit 16. After a desired number of translations are completed for a core sample slice, the sample is indexed one slice-width through the X-ray fan beam to place the next adjacent sample slice within the path of the X-ray fan beam. In this manner, a 3-D tomographic presentation is made of the entire sample, as shown at step 5 in FIG. 1, by compositing the cross-sectional view of each of the scan slices. Such a CT scanning system, while not forming a part of the present invention, is used in accordance with the method of the present invention to quantify the barite content at step 6 in a core sample for use in identifying the correct porosity in step 7 of such core sample.

A particularly suitable X-ray scanner used for CT imaging is the Elscint Exel 2002 translate-rotate body scanner with a Telefunken C-6000 stationary anode-cathode X-ray tube and 280 cadmium tungstate scintillation detectors coupled to solid state photodiodes. The peak X-ray acceleration voltage is 140 kV at 40.0 mA. The spatial resolution is 20 line pairs per cm. The pixel (picture element) size at Zoom 1 ($512 \times 512$) ranges from 0.265 mm to 0.94 mm and at Zoom 4 ($512 \times 512$) ranges from 0.065 mm to 0.23 mm varying with scan and circle diameter and reconstruction zoom factor.

The recorded digital image is composed of individual image units arranged in a matrix. Computer tomography images consist of maps of linear X-ray attenuation coefficients within the object being imaged. On standard black and white images, each pixel contains discrete information that corresponds to a spectrum of tonal values on a greyness scale ranging from black (DN=255) to white (DN=0). Similarly, CT image pixels are assigned density values on the Hounsfield scale ranging from low density ($-1000$) to high density ($+3095$).

The Elscint software package VOLUME CALC assigns pixels to groups of similar density through classification algorithms. Image interpretation consists of assigning significance to each group or class according to its density range. Cutoff values for each component analysis (mud, matrix, pore) can be interactively selected through the use of a cursor along with CT number display. For each component analyzed, the integrated volume can be calculated throughout the "sliced" core block.

Image CT density values for each pixel must fall within the $-1000$ to 3095 range. Off-scale high density values are assigned values of $-1000$ and appear as black pixel blocks within white or grey pixel zones. This was corrected by calibrating with a TEFLON standard that moved the center of the Hounsfield scale by 750 units in order to permit on-scale readings of the dense material. The X-ray CT scanner is recalibrated with reference to water (0) between samples.

The three main rock constituents analyzed (rock matrix, pore, mud) register best on tomographic images when scaled to a TEFLON standard reference of 750 CT units. This recalibration minimizes both beam hardening artifacts and high density material volume shrinkage. Several artificial image effects may be created during the scanning and data reconstruction procedures. Beam diffraction effects register as hard, straight, tangential lines off the core edge.

Extreme diffraction around the core may also register as a halo surrounding the core edge. Both these effects can be reduced by lowering the CT calibration center (Hounsfield units) and window values. Average calibration center and window CT values used were $-150$ and 650, respectively, but may be varied on each core sample to optimize image quality.

VOLUME CALC will calculate the volume of a component specified by a CT density pair. The density pair for each component analyzed is interactively selected by using the cursor and joystick. A CT density scale is recorded for each sample analyzed because CT density values may vary from sample to sample and scan to scan.

Volumetric calculations on four mud-invaded core samples for the rock matrix, pore space and mud solid component fractions are shown in the following TABLE. Differences in total volume are due to irregular edges of the core ends.

While an irregularly shaped core sample may be measured by standard caliper methods, it produces a distorted CT image due to edge effects and should be edited out before volume calculations.

ite and remaining minerals in said core sample, said barite being of a higher grain density than said remaining minerals.

3. The method of claim 2 wherein said step of calibrating said X-ray scanning includes adjusting of a computed tomographic number (CT) scale in Hounsfield units to a zero level based on a numerical measure of an X-ray absorption of polytetrafluroethylene, which is denser than a water standard.

4. A method of determining the porosity and drilling mud invasion of a core sample from a subterranean formation comprising the steps of:

TABLE

| | VOLUME BY CT-IMAGE (cc) | | | CALIPER VOLUME | CT-IMAGE DENSITY WINDOW | | | |
|---|---|---|---|---|---|---|---|---|
| CORE NO. | MATRIX | PORE | MUD | V. BULK (cc) | PORE | MATRIX | MUD | STANDARD |
| 1 | 205 | 25 | 12 | 420.24 | −750 to −470 | −469 to 899 | 900 to 2700 | −650 |
| 2 | 485 | 75 | 21 | 929.82 | −830 to −261 | −260 to 239 | 240 to 2700 | −750 |
| 3 | 772 | 59 | 3 | 997.50 | −830 to −380 | −379 to 195 | 196 to 2700 | −750 |
| 4 | 969 | 116 | 21 | 1282.87 | −380 to −330 | −329 to 119 | 120 to 2700 | −750 |

We claim:

1. A method for identifying the porosity and mud invasion of a core sample from a subterranean formation, comprising the steps of:
   (a) removing mud filtrate from said core sample,
   (b) measuring pore volume of said core sample after the mud filtrate removal,
   (c) measuring bulk volume of said core sample,
   (d) measuring mud solid volume in said core sample after said mud filtrate removal, and
   (e) determining the porosity of said core sample from said pore volume, bulk volume and mud solid volume measurements.

2. The method of claim 1 wherein said step of measuring mud solid volume in said core sample comprises the steps of:
   (a) scanning said core sample with X-rays,
   (b) calibrating said scanning of said core sample to a density scale based on a presence of barite in said core sample,
   (c) producing computed tomographic images from said scanning of said core samples, and
   (d) determining the mud solid volume in said core sample from a density contrast created in said computed tomographic images by the presence of bar- (a) supplying gas to said core sample at a first pressure,
   (b) allowing said gas to expand from said core sample until equilibrium is reached,
   (c) measuring gas volume that expands from said core sample,
   (d) measuring a second pressure in the core sample after said gas has expanded,
   (e) determining pore volume of said core sample from said first and second pressures and measured volume,
   (f) measuring bulk volume of said core sample,
   (g) determining the porosity of said core sample from a ratio of said pore volume to said bulk volume,
   (h) producing computed tomographic images of said core sample,
   (i) identifying a concentration of drilling mud solid in said core sample based on a density effect of said drilling mud solid on said computed tomographic images, and
   (j) correcting the porosity determination for volumetric concentration of said mud solids in pore spaces of said core sample.

* * * * *